United States Patent [19]

Greenberg

[11] Patent Number: 5,409,493
[45] Date of Patent: Apr. 25, 1995

[54] SINGLE-HANDED SURGICAL DRILL DEPTH GUIDE

[76] Inventor: Alex M. Greenberg, 145 W. 67th St., New York, N.Y. 10023

[21] Appl. No.: 919,783

[22] Filed: Jul. 24, 1992

Related U.S. Application Data

[63] Continuation-in-part of Ser. No. 719,178, Jun. 21, 1991, Pat. No. 5,133,720, which is a continuation-in-part of Ser. No. 552,703, Jul. 13, 1990, Pat. No. 5,026,376.

[51] Int. Cl.$^6$ .............................................. A61F 17/00
[52] U.S. Cl. ........................................ 606/96; 606/86; 606/79
[58] Field of Search .................. 606/79, 80, 86, 96, 606/97, 98, 102, 104, 119, 55, 87, 108, 162

[56] References Cited

U.S. PATENT DOCUMENTS

| | | |
|---|---|---|
| 2,427,128 | 9/1947 | Ettinger . |
| 2,494,229 | 1/1950 | Collison . |
| 3,530,860 | 9/1970 | Majoros ........................ 606/108 X |
| 3,752,161 | 8/1973 | Bent . |
| 3,835,860 | 9/1974 | Garretson . |
| 3,897,786 | 8/1975 | Garnett et al. ................. 606/108 X |
| 3,913,584 | 10/1975 | Walchle et al. ................ 606/108 X |
| 4,586,497 | 5/1986 | Dapra et al. . |
| 4,708,139 | 11/1987 | Dunbar, IV ......................... 606/96 |
| 4,739,751 | 4/1988 | Sapega et al. . |
| 4,813,407 | 3/1989 | Vogen . |
| 4,883,048 | 11/1989 | Purnell et al. . |
| 5,013,318 | 5/1991 | Spranza, III ........................ 606/102 |
| 5,026,375 | 6/1991 | Linovitz et al. . |
| 5,197,967 | 3/1993 | Wilson ............................... 606/79 |

FOREIGN PATENT DOCUMENTS

| | | |
|---|---|---|
| 645252 | 7/1962 | Canada . |
| 2598311 | 11/1987 | France . |
| 2903471 | 8/1979 | Germany . |
| 649420 | 2/1979 | U.S.S.R. . |

OTHER PUBLICATIONS

Oral and Maxillofacial Traumatology, "Internao Fixation of Zygomatic and Midface Fractures by Means of Miniplates and Lag", pp. 177–186, Quintessence Publ., Inc. 1986.

Kruger et al, Oral and Maxillofacial Traumatology, vol. 2, p. 181, Fig. 10, 4–6 (1986), "Summary of Surgical Technique", catalogue from Synthes Maxillofacial, Paoli, Pa., published 1992.

*Primary Examiner*—Sam Rimell
*Attorney, Agent, or Firm*—Meltzer, Lippe, Goldstein

[57] ABSTRACT

A surgical drill guide for treating fractures in the craniomaxillofacial region is disclosed. The drill guide includes a telescopic sleeve having an inner telescoping segment slidably mounted within an outer telescoping segment. The telescopic sleeve also has a through-going bore which connects a first opening at an end of the outer telescoping segment with a second opening at an end of the inner telescoping segment. The bore is dimensioned for slidably receiving a drill bit or other instrument therein. The telescopic sleeve is mounted on a handle which includes a trigger. The trigger is provided for slidably retracting the inner segment into the outer segment to expose a preselected length of a drill bit or other instrument inserted through the bore of the sleeve.

25 Claims, 13 Drawing Sheets

SINGLE-HANDED SURGICAL DRILL DEPTH GUIDE

This is a continuation-in-part of application Ser. No. 07/719,178, filed Jun. 21, 1994, now U.S. Pat. No. 5,133,720, which is a continuation-in-part of application Ser. No. 07/552,703, filed Jul. 13, 1990, now U.S. Pat. No. 5,026,376.

FIELD OF THE INVENTION

The present invention relates to a surgical drill guide which may be adjusted and operated with a single hand. More particularly, the invention relates to a surgical instrument which acts as a drill depth guide for the surgical drilling of anatomical bone exposed by an incision. The inventive device is particularly useful for the treatment of bone fractures in craniomaxillofacial regions or any other anatomic bone structure.

BACKGROUND OF THE INVENTION

The treatment of bone fractures in craniomaxillofacial regions generally proceeds by reducing the fractured bones to their anatomically correct positions, and thereafter fixing the bones in place. The bones may be fixed in place either by interosseous wiring, or by the technique of miniplate osteosynthesis. In either case, holes must be drilled in the bone structure for receiving the interosseous wire or screws for holding the miniplates to the bone.

In the drilling of holes into the bone structure, great care must be taken to ensure that the holes are drilled at precisely the correct place and to precisely the correct depth. If the holes are not drilled at the correct location, strain may be transmitted by screws to the surrounding bone structure. This may cause the bone to resorb in the vicinity of the screws, with the loosening of the hardware.

Similarly, complications, such as blindness, extraocular muscle dysfunction, retinal or corneal damage, and severe tissue trauma could result if the depth of holes is not gauged accurately. Accordingly, it is desirable during the drilling procedure to use an instrument which will prevent the surgeon from drilling too deeply into bones of craniomaxillofacial regions. Furthermore, it is also desirable to control the angle of the drilling to permit greater flexibility in the placement of implants. For example, if screws are to be placed into the frontal bone they are preferably inserted at a downward slanting angle with respect to the forehead. This ensures that neither the screws nor the drill bit enters the orbit. See M. Zide, "The Placement of Screws Above the Zygomaticofrontal Suture," 48 J. Oral & Maxillofacial Surg. 813–816 (1990).

Figure 1:
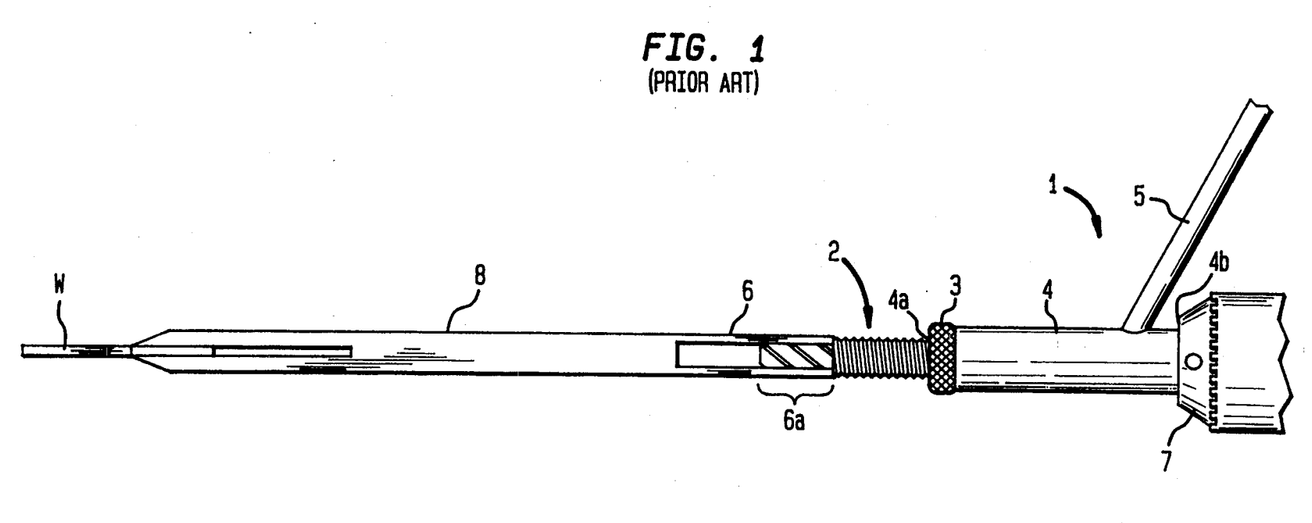
FIG. 1 illustrates a prior art drill guide.

A prior art drill guide, for controlling the angle and the depth of a hole drilled into anatomical bone, is disclosed in a catalog published in 1992 by Synthes Maxillofacial, a surgical supply company located in Paoli, Pa. This drill guide 1 is depicted in FIG. 1. The drill guide 1 has a threaded inner sleeve 2 which is screwed into a first opening 4a of an outer sleeve 4. By rotating the inner sleeve 2 with respect to the outer sleeve 4, the inner sleeve 2 may be extended from, or retracted into, the outer sleeve 4. A knurled nut 3 is provided which may be loosened to permit the rotation of the inner sleeve 2. After the inner sleeve 2 is adjusted to a desired length from the outer sleeve 4, the knurled nut 3 may be tightened to prevent rotation of the inner sleeve 2.

The outer sleeve 4 is attached to, and integral with, a handle 5. The outer sleeve 4 and handle 5 are connected so as to form an obtuse angle.

Figure 2:
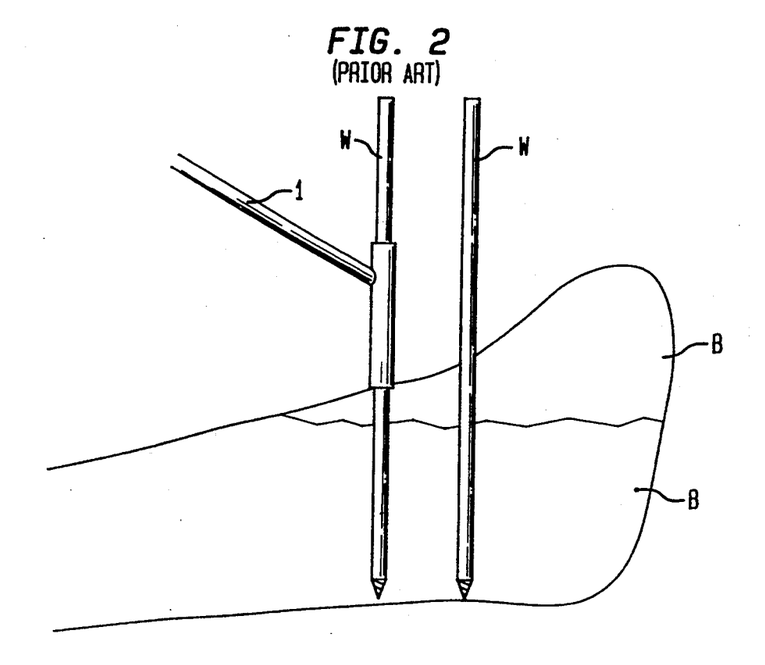
FIG. 2 illustrates a surgical procedure for drilling holes into bone with the prior art drill guide of FIG. 1.

Such a drill guide 1 is useful in a variety of surgical operations. An exemplary surgical operation using the drill guide 1 proceeds as follows. An incision is made in the region of the fracture, the skin is retracted, and the bones are reduced to their correct anatomical positions. One or more threaded guide wires W are then inserted into the bones B, as depicted in FIG. 2, using a small diameter drill guide 1. The depth to which the guide wire W is inserted into the bones B is then measured by sliding a depth gauge sleeve 8 (FIG. 1) over the exposed portion of the guide wire W.

Knowing the depth of penetration of the guide wire W, the drill guide 1 may be adjusted so as to limit the drilling of a hole to a desired depth. A cannulated drill bit 6 (i.e., a drill bit with a central bore) is inserted into a second end 4b of the outer sleeve 4 until the quick coupling 7 of the drill abuts against the second end 4b of the outer sleeve 4 as depicted in FIG. 1. While the drill guide 1 is held in this position with one hand, the depth gauge sleeve 8 is inserted over the exposed portion of the drill bit 6a. Using the other hand, the knurled nut 3 is loosened, and the inner sleeve 2 rotated until the length of the exposed portion of the drill bit 6a equals the desired drilling depth. The knurled nut 3 is then tightened so that the inner sleeve 2 does not retract into, or extend from, the outer sleeve 4 during the drilling of the hole.

Figure 3:
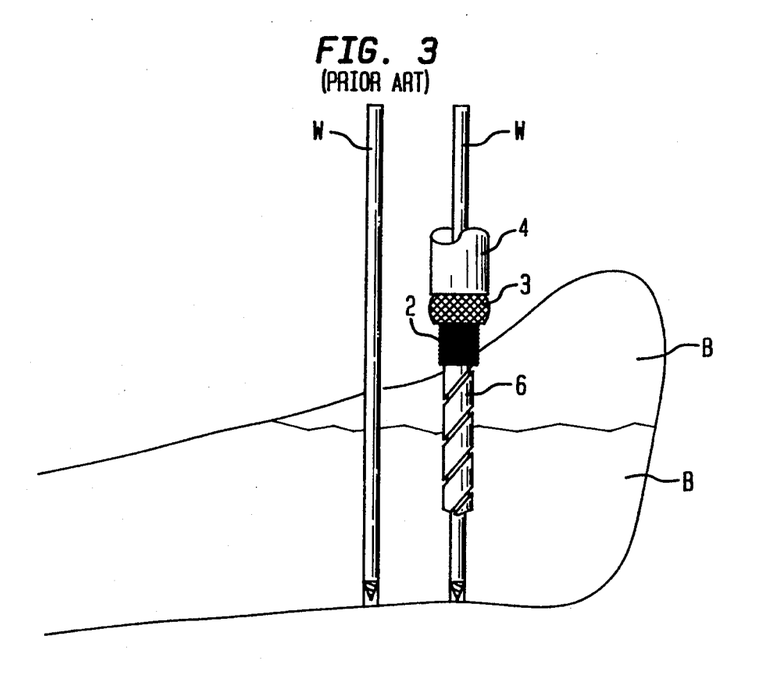
FIG. 3 further illustrates a surgical drilling procedure using the prior art drill guide of FIG. 1.

The adjusted drill guide 1 may then be inserted over the guide wire W until the inner sleeve 2 contacts the bone B, as depicted in FIG. 3. The cannulated drill bit 6 is inserted into the second end 4b of the outer sleeve 4 of the drill guide 1 over the guide wire W. The drill is then operated to drill into the bones B until the quick coupling 7 of the drill abuts against the second end 4b of the outer sleeve 4. Thus, the drill guide 1 acts as a stop, preventing the drilling of holes deeper than the length of the exposed portion of the drill bit 6a which protrudes from the drill guide 1 when the quick coupling 7 abuts against the second end 4b of the outer sleeve 4.

After the hole is drilled to the correct depth, a surgical screw is inserted into the hole and the guide wire is removed. The screws may secure an implant, such as a miniplate, to the bone structure. The miniplate holds the bone structure together so that it can heal.

Another special drill guide has been proposed for use in performing miniplate osteosynthesis in the orbital region. See, e.g., FIGS. 10.4–6, appearing on page 181 of Krüger et al, *Oral and Maxillofacial Traumatology*, Vol. 2, Quintessence Pub. Co., Inc., Chicago (1986). The special orbital drill guide consists of a handle, a curved C-shaped arm attached to the handle, and a plunging mechanism also attached to the handle. The plunging mechanism consists of an outer sleeve and inner sleeve, each of which has a through-going bore. The inner sleeve is slidably mounted within the outer sleeve, whereby it functions as a plunger. Both inner and outer sleeves are mounted on the handle in line with the C-shaped member.

To employ the special orbital drill guide, an assistant uses malleable retractors to retract the sides of the incision. With the surgeon holding the drill guide by the handle, the C-shaped arm is inserted into the incision and manipulated until it is positioned on and behind the orbital bone. The tip of the C-shaped arm is thus able to act as a protective stop behind the bone to be drilled.

The outer sleeve is aligned with one of the holes in the miniplate and the inner sleeve is plunged forward through the outer sleeve until it comes in contact with a hole of a miniplate. Thereafter, a drill bit is inserted through the bore of the inner sleeve and a hole is drilled through the orbital bone in line with the hole of the miniplate. The tip of the C-shaped arm prevents the drill bit from penetrating too deeply into the ocular region.

The prior art drill guides, while useful, are not entirely satisfactory for their above-described procedures. The first prior art drill guide requires more than one hand to adjust the drilling depth, i.e., one hand to turn the knurled nut or inner sleeve and one hand to grasp the handle of the drill guide. Second, a separate depth gauge is required for adjusting the drilling depth of this drill guide.

The second prior art drill guide also has disadvantages. First, the special orbital drill guide, particularly its plunging mechanism, is difficult to manipulate and keep in place when drilling bones. Second, the C-shaped arm is not very well adapted to go around the orbital bone and act as a protective stop. The hemispherical shape of the arm extends too far into the orbit creating pressure on the eyeball which can cause contusion of extraocular muscles and retinal detachment. Third, the ocular drill guide may only be used in regions where the surgeon can position the C-shaped arm behind the bone to be drilled. Furthermore, the drill bit penetrates entirely through the bone to the other side. This is disadvantageous when it is desirable to drill less than entirely through the bone, such as when drilling near the far cortex.

Accordingly, it is an object of the present invention to provide a surgical instrument which will act as a drill guide for drilling anatomical bones and which can be adjusted with a single hand.

It is a further object of the present invention to provide a surgical drill guide which permits the drilling of a bore into anatomical bones at a controlled angle.

It is yet another object of the present invention to provide a drill guide which can limit the drilling of holes to depths less than or equal to the entire thickness of the bone.

It is yet a further object of the present invention to provide a drill guide which does not require access to opposite sides of the bones to be drilled.

SUMMARY OF THE INVENTION

The present invention achieves these and other objects by providing a surgical drill guide which has a telescopic sleeve with an inner telescoping segment slidably mounted within an outer telescoping segment. The telescopic sleeve has a bore which passes entirely through the inner and outer telescoping segments and which connects an opening at an end of the outer segment with an opening at an end of the inner segment. The bore is dimensioned so that a drill bit or other instrument may be inserted through the telescopic sleeve.

The telescopic sleeve is mounted to a handle which includes a trigger. The trigger is provided for retracting the inner telescoping segment into the outer telescoping segment, thereby exposing a preselected amount of a drill bit inserted through the sleeve.

The length of the drill bit which can be inserted through the sleeve may be limited to a particular length. For example, a drill bit may be inserted into the opening at the outer segment end and through the bore until the quick coupling of the drill, to which the bit is attached, contacts the outer segment. Using the trigger, the inner segment may then be retracted to expose a preselected amount of the drill bit protruding from the opening at the inner segment end of the sleeve.

Illustratively, the trigger and handle are each connected to a different telescoping segment. In an embodiment, the trigger is also pivotally connected to the handle for a scissoring movement therewith. Thus, when the trigger is urged towards the handle, the inner segment slides into the outer segment. In an alternative embodiment, the trigger and handle are not connected together. In this embodiment, the trigger may be urged towards the handle by a simple sliding movement to retract the inner segment into the outer segment.

Optionally, a depth scale may be provided on the outer surface of the sleeve which may be used to calculate the drilling depth of the drill bit. Preferably, this scale is provided on the inner telescoping segment. Other options include, a spring for biasing the sleeve to its fully extended position, and a fastener, such as a set screw, for retaining the length of the sleeve in a fixed position during the drilling of holes.

DETAILED DESCRIPTION OF THE INVENTION

Figures 4, 4A:
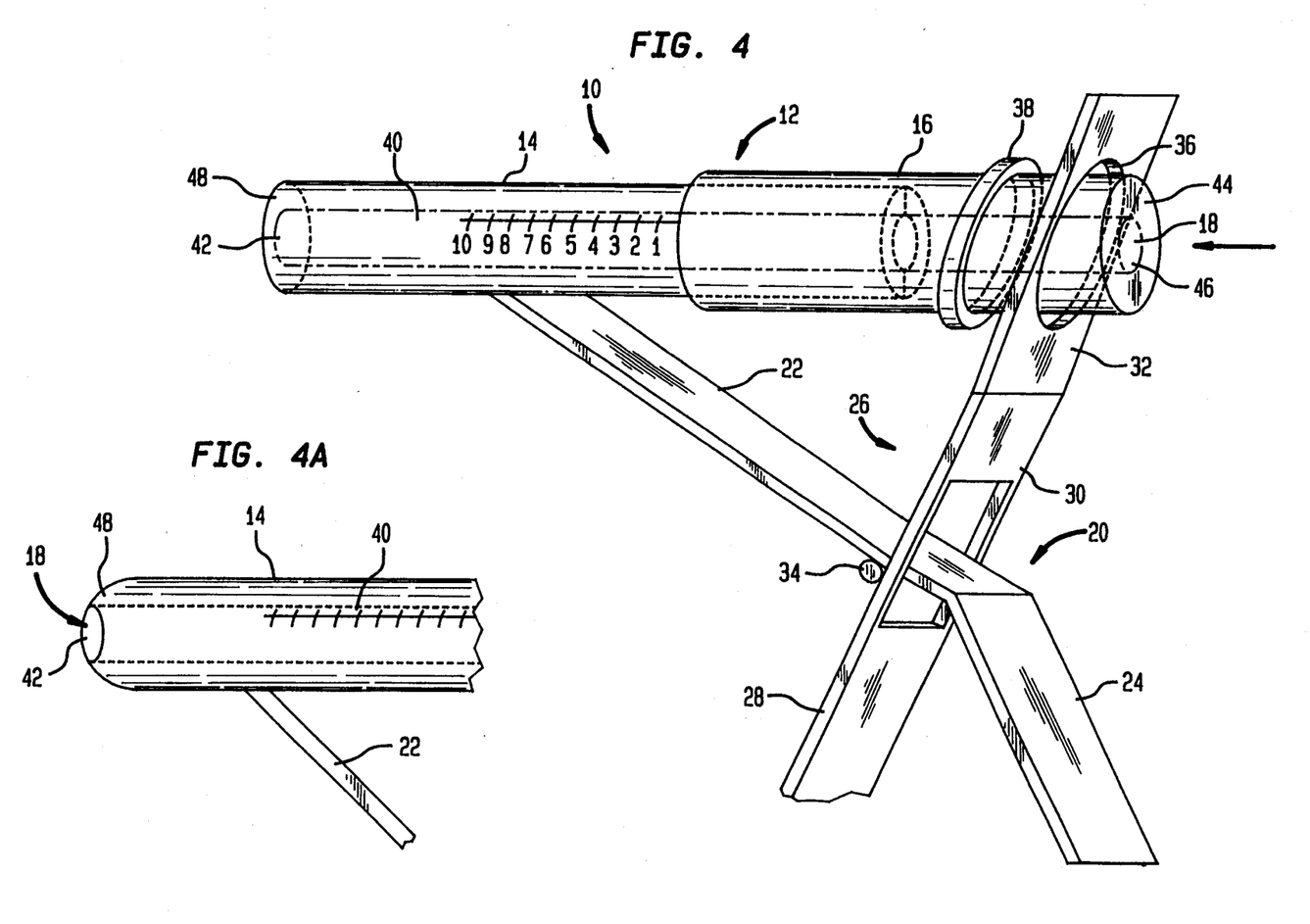
FIG. 4 illustrates one embodiment of the surgical drill guide according to the invention.
FIG. 4A illustrates a variation of the inventive surgical drill guide of FIG. 4.

A drill guide 10, according to one embodiment of the invention, is depicted in FIG. 4. The drill guide 10 has a telescopic sleeve 12 which includes an inner telescoping segment 14 and an outer telescoping segment 16. The inner segment 14 is positioned within the outer segment 16 and may slidably retract or extend therefrom.

The sleeve 12 has a bore 18 which passes through both segments 14 and 16. The bore 18 is designed to receive a drill bit or other instrument therethrough.

As depicted, a handle 20 is connected to the inner segment 14. The handle 20 includes a member 22 which is connected to the inner segment 14 and to a grip 24. A segmented trigger 26 is also provided with a lever arm 28 attached to a connecting member 30 which is also attached to a contact plate 32. As shown in FIG 4, the lever arm 28 is illustratively connected by a hinge or pivot 34 to the member 22. The handle 20 and trigger 26 are thus capable of a scissoring movement.

The contact plate 32 has a slot 36 into which the outer segment 16 is positioned. The outer segment 16 also has a contact shoulder or ring 38 on its outer surface. The contact ring 38 has a diameter which is greater than the width of the slot 36 so that it cannot be inserted therein.

The inner segment 14 illustratively is scored with markings 40. These markings form a measuring scale or gauge useful in measuring the depth that a drill bit inserted through the sleeve 12 may penetrate into the bone.

The surgical drill guide 10 is used as follows. An incision is made in the region of the fracture and the bones are reduced to their correct anatomical positions. A threaded guide wire is inserted into the bone. The threaded guide wire may be inserted using a drill guide 10 having a bore 18 dimensioned specifically for the guide wire. Next, the drilling depth of the hole is determined. This may be accomplished by sliding a measuring gauge over the guide wire to measure the depth to which it is inserted. Thereafter, the surgeon grasps a drill guide 10 which has a bore 18 dimensioned for receiving a drill bit. While holding the drill guide 10 with one hand by its grip 24, the surgeon, using a finger, depresses the lever arm 28 so that it is brought into proximity with the grip 24. This causes the contact plate 32 to press against the contact ring 38 thereby telescopically retracting the inner segment 14 into the outer segment 16. The surgeon squeezes the lever arm 28 until the telescopic sleeve 12 is the correct length, i.e., the length of a drill bit less the desired drilling depth. The surgeon can utilize the markings on the outer sleeve to determine the correct amount that the inner segment 14 should be retracted into the outer segment 16. Alternatively, the surgeon may insert a drill bit a far as possible (e.g., until the quick coupling of the drill contacts the end 44 of the outer segment 16) into the opening 46. Thereafter, the surgeon adjusts the length of sleeve 12 by measuring the exposed portion of the drill bit protruding from an opening 42 at the end 48 of the inner segment 14.

After the drill guide 10 is correctly adjusted, it is inserted into the incision, over the guide wire until the end 48 of the inner segment 14 contacts the bone. A cannulated drill bit is then inserted into the bore 18 over the guide wire. Once the drill bit is inserted, the surgeon drills into the bone until the quick coupling of the drill contacts the end 44 of the outer segment 16. The drill guide 10, by virtue of being positioned between the bone and the quick coupling, acts as a stop. This is because the opening 46 is only large enough to accept the drill bit. The end 44 limits the length of the drill bit inserted into the bore 18 by preventing the insertion of the quick coupling into the opening 46. Thus, only the portion of the bit, protruding from the end 48 of the inner segment 14 is permitted to penetrate into the bone.

After the hole is drilled, the drill bit is withdrawn and a self-tapping surgical screw is inserted through the bore 18 of the sleeve 12 and screwed into the bone. Preferably, the screw is first secured to a screwdriver which is then inserted through the bore 18 and over the guide wire. Because the markings on the inner sleeve are calibrated against the overall length of the sleeve 12, the surgeon can easily determine the length of drill bit protruding from the end 48 of the sleeve 12 and thus, the depth of the hole. This enables the surgeon to select a screw of the precise required length. In addition, the drill guide 10 may be used for tapping or countersinking the hole prior to inserting the screw. In such a case, the appropriate instrument, e.g., tap, countersink, etc., may be inserted into the bore 18 and thereby guided by the drill guide 10. After the screw is inserted, the guide wire is withdrawn. Alternatively, the drill guide may be used without a guide wire.

Figure 5:
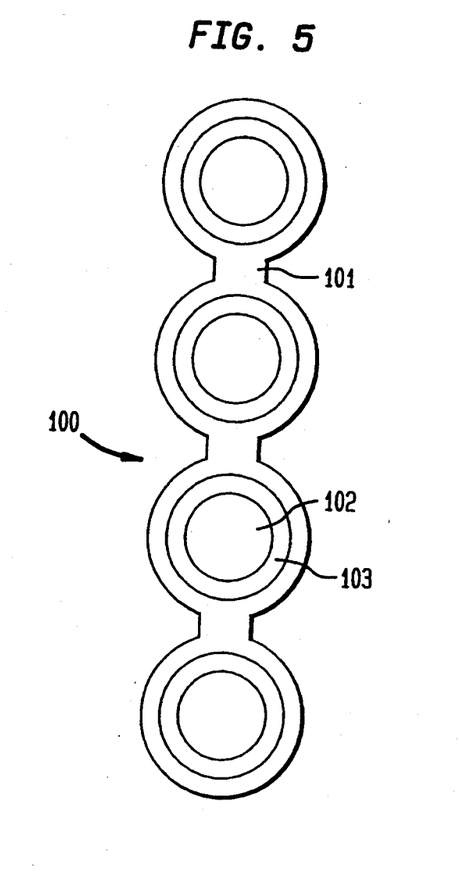
FIG. 5 illustrates a miniplate for use in securing bone fragments together.

The inventive drill guide 10 may also be used in the technique of miniplate osteosynthesis. Referring to FIG. 5, a greatly enlarged miniplate 100 which is useful in the treatment of craniomaxillofacial fractures is shown. Numerous different configurations of the miniplate may be used depending on the size and shape of the reduced bone structure. The miniplate 100 is just one example of a suitable miniplate. The miniplate 100 consists of a chain-like body 101 having holes 102 therein. Each of the holes 102 is countersunk with a beveled edge 103 so that the holes 102 are adapted to receive surgical screws (not shown) and to retain the reduced bone structure in place until the bone heals.

In the technique of miniplate osteosynthesis, the incision is made in the region to which the miniplate 100 is to be secured. The bone fragments are reduced to their correct anatomical positions and the miniplate 100 is positioned on the bone fragments. The drill guide 10 is then adjusted to a preselected length and positioned over the first hole 102 of the miniplate. As depicted in FIG. 4A, the end 48 of the inner segment 14 may be chamfered so that it fits snugly into the countersunk holes 102 of the miniplate 100. In this manner, the miniplate 100 may be held in place by the drill guide 10 while the hole is drilled. After the hole is drilled, a screw is inserted to secure the miniplate 100 to the bone. When this entire procedure is completed for one hole 102, the surgeon moves to the next hole 102 of the miniplate 100 and repeats the procedure until the miniplate 100 has been properly secured into position on the reduced bone structure.

Figures 6, 6A:
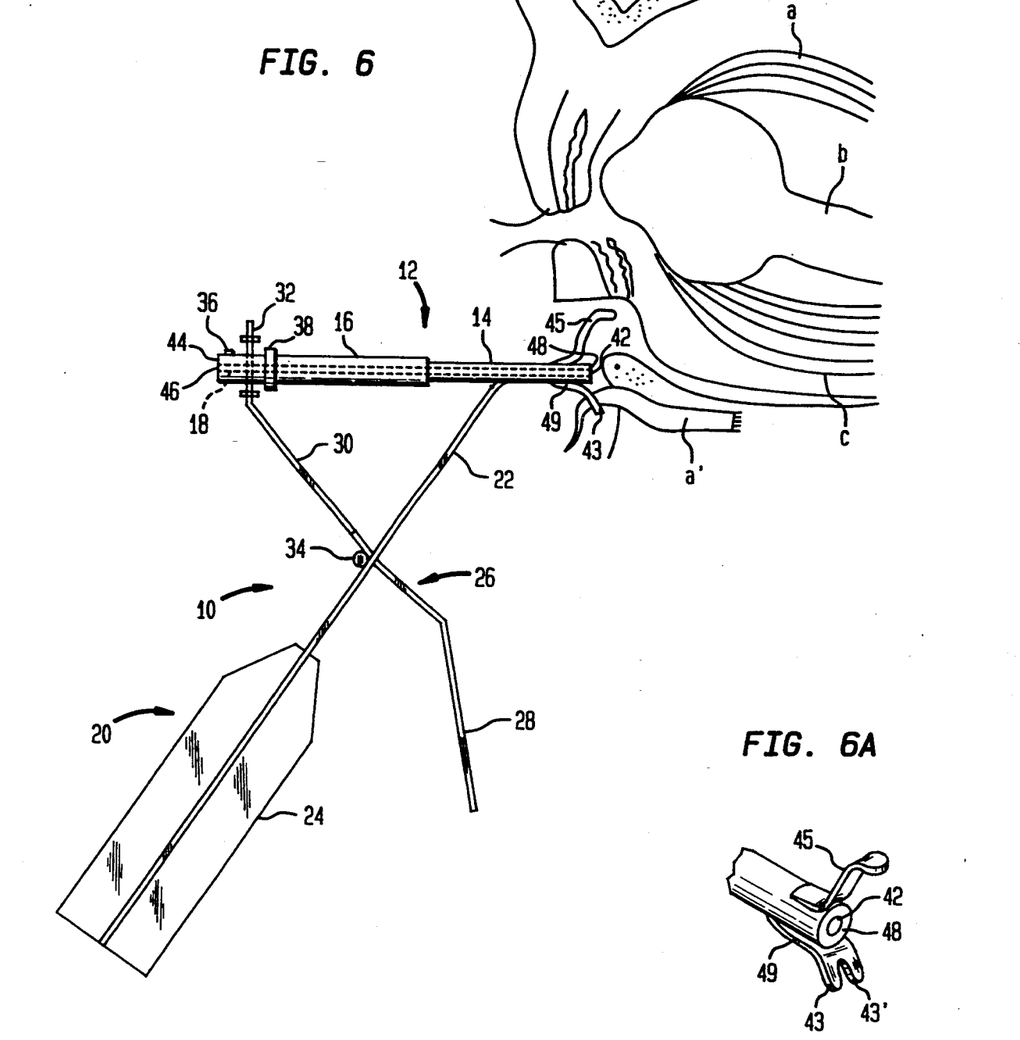
FIG. 6 illustrates the inventive surgical drill guide of FIG. 4 with optional retractors in an infraorbital application.
FIG. 6A illustrates the optional retractors of the inventive surgical drill guide of FIG. 6 in greater detail.
Figure 7:
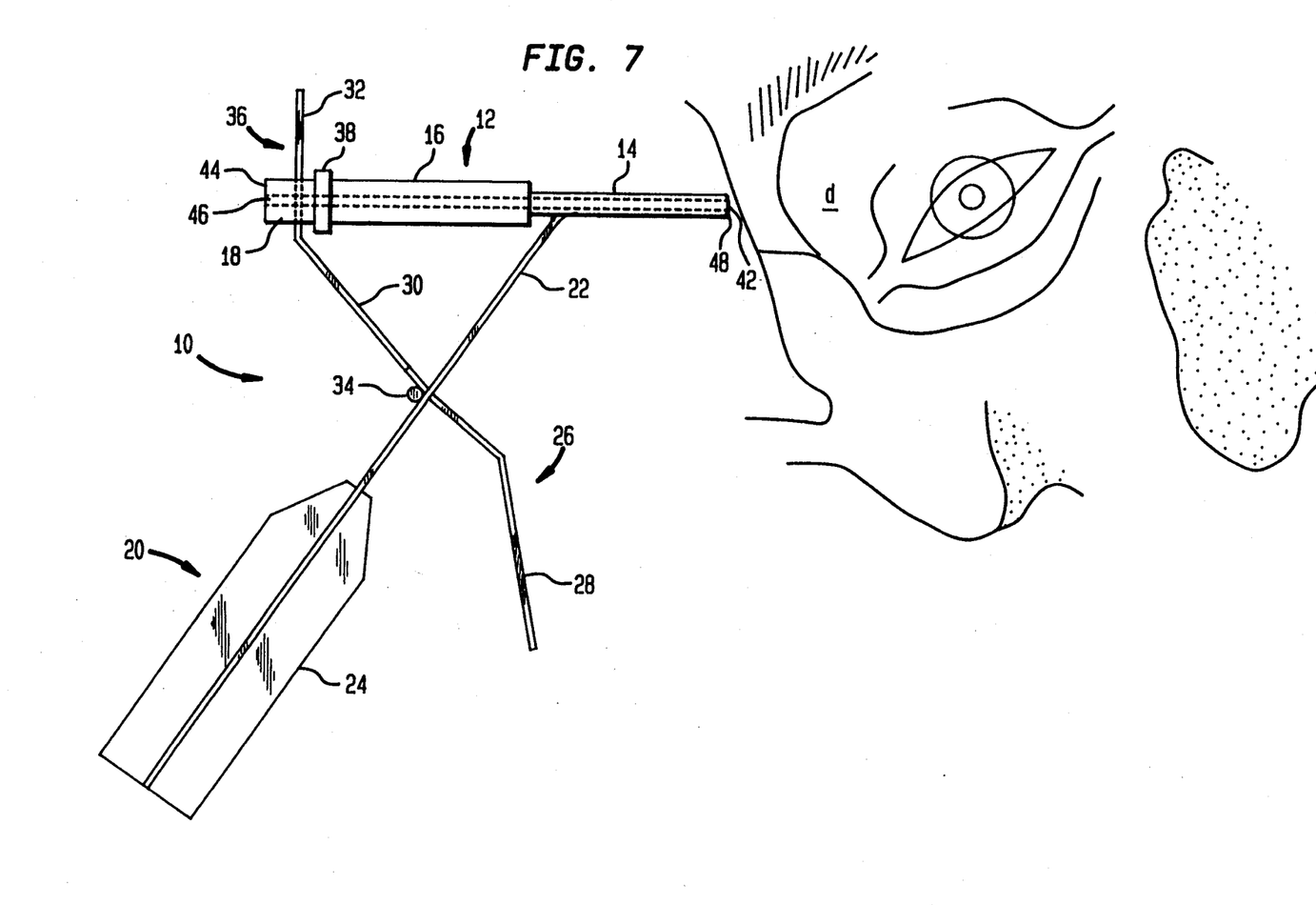
FIG. 7 illustrates the inventive surgical drill guide of FIG. 4 in a zygomaticofrontal application.

FIG. 6 illustrates the use of device 10 in the infraorbital region. In FIG. 6, a designates the superior rectus muscle, b designates the optic nerve, and c designates the inferior rectus muscle. The drill guide of FIG. 6 is shown with optional major 45 and minor 49 retractors attached at the end 48 of the inner segment 14. The minor retractor 49 extends in a direction substantially opposite to the major retractor 45. When inserted into an incision (as depicted in FIG. 6) the major 45 and minor 49 retractors cooperate so as to provide an opening effect thereby retracting the sides of an incision. As depicted in FIG. 6, the minor retractor 49 may be shaped so as to bridge any nerve in the vicinity of the incision, such as the infraorbital nerve designated by a'. As depicted in FIG. 6A, the minor retractor 49 is bifurcated with two fingers 43, 43' so that the minor retractor may be inserted around a nerve. In FIG. 7, the inventive device 10 is illustrated as being used in the zygomaticofrontal region which is designated by d.

Figure 8:
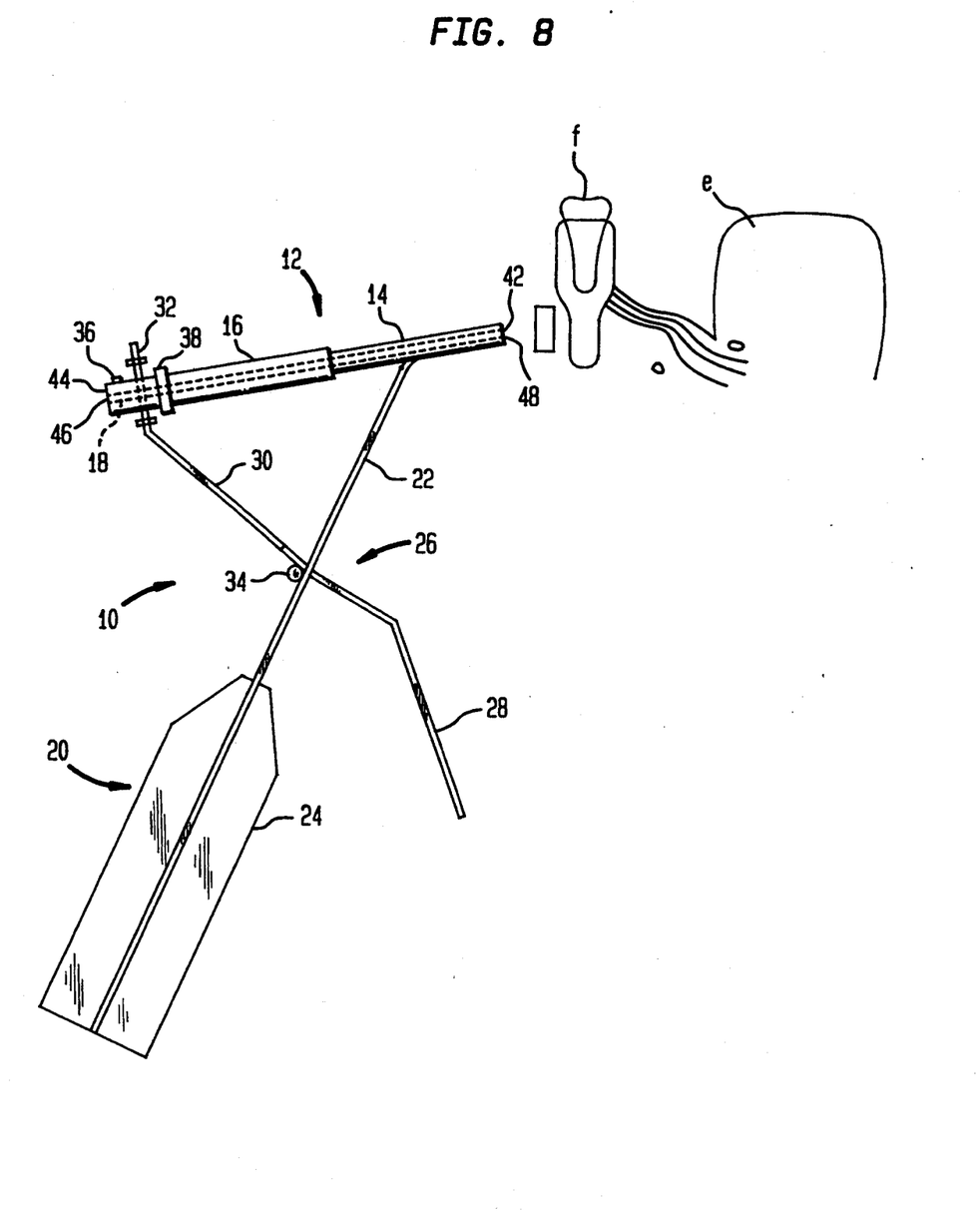
FIG. 8 illustrates the inventive surgical drill guide of FIG. 4 in a mandibular application.
Figure 9:
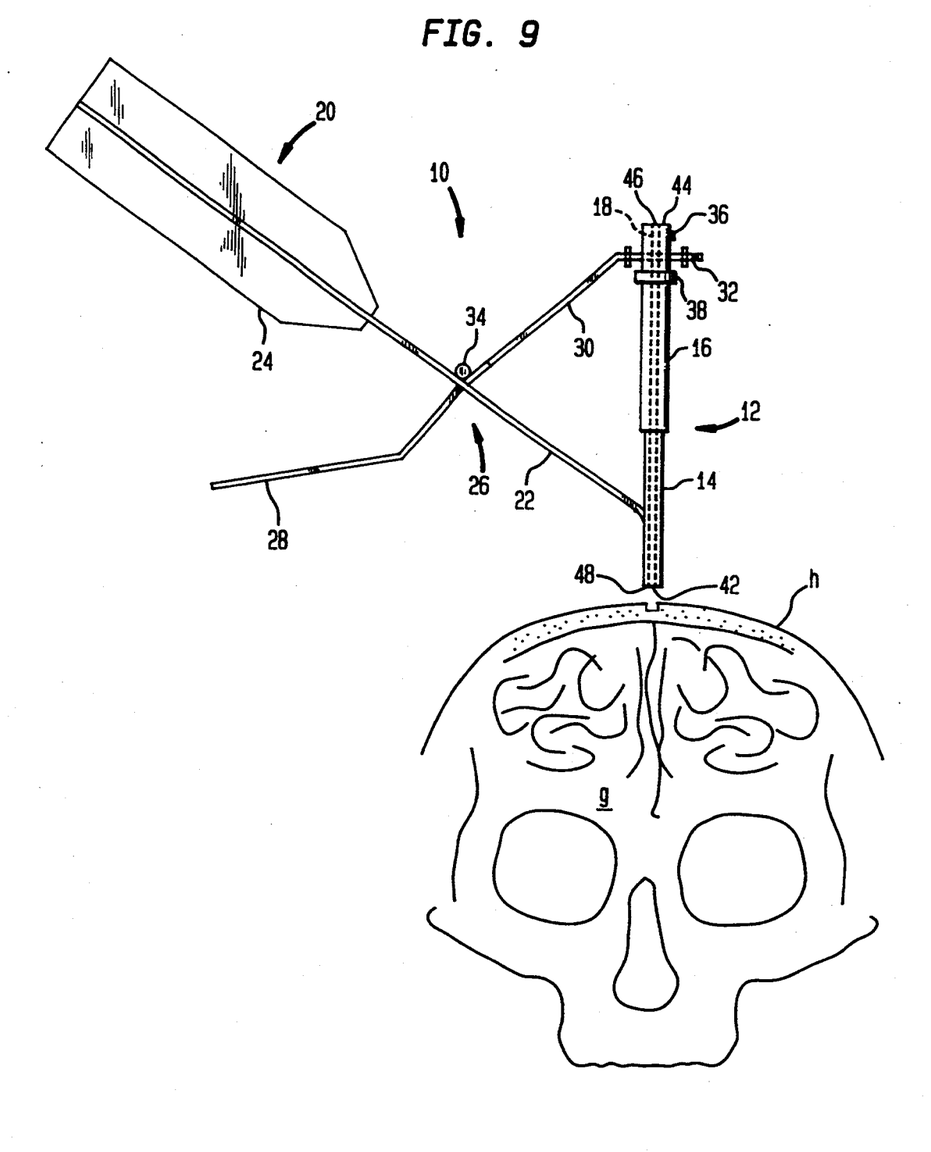
FIG. 9 illustrates the inventive surgical drill guide of FIG. 4 in a cranial application.

The device 10 may also be used in the mandibular and cranial regions and such applications are illustrated in FIGS. 8 and 9 respectively. In FIG. 8, f designates the mandible in the coronal region with the tongue being shown as e. In FIG. 9, g designates the brain within the cranium h. The label i designates a hole drilled using the device which does not penetrate entirely through the cranium h. The device 10 is particularly suited for applications in which it is desired to drill into the cranium h no deeper than within 5 mm of the inner side of the cranium h.

Figures 10, 10A:
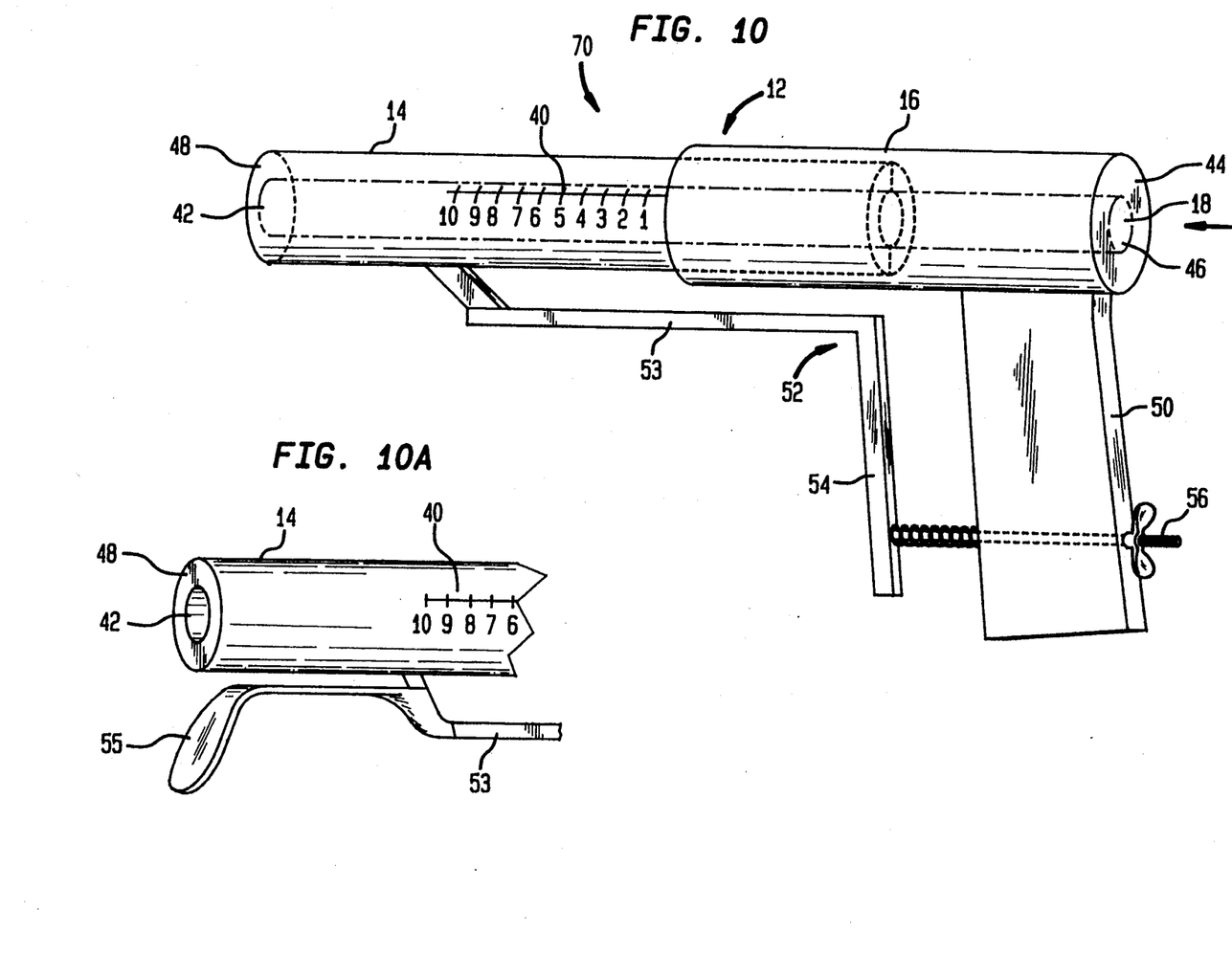
FIG. 10 illustrates a second embodiment of a surgical drill guide according to the invention.
FIG. 10A illustrates an optional retractor attached to the inventive surgical drill guide of FIG. 10.

FIG. 10 illustrates another embodiment of the drill guide 70 according to the invention. In this embodiment, the handle 50 is attached to the outer segment 16. The trigger 52 is an approximately L-shaped member having a long leg 53 attached to the inner segment 14 and a short leg 54 which extends in the vicinity of the handle 50. In this embodiment, the inner segment may be retracted into the outer segment 16 by sliding the short leg 54 towards the handle 50. As shown in FIG. 10A, retractors, such as the major retractor 55, may optionally be attached to the end of the long leg 53 opposite the short leg 54. The drill guide 70 is also shown with a set screw 56 which is capable of retaining the inner segment 14 in its adjusted position while the surgeon operates the drill. In this case the inventive instrument is self-retaining. In the alternative, a ratchet mechanism can be used for adjusting the length of the sleeve 12 and for retaining the inner segment 14 in its adjusted state.

Figure 11:
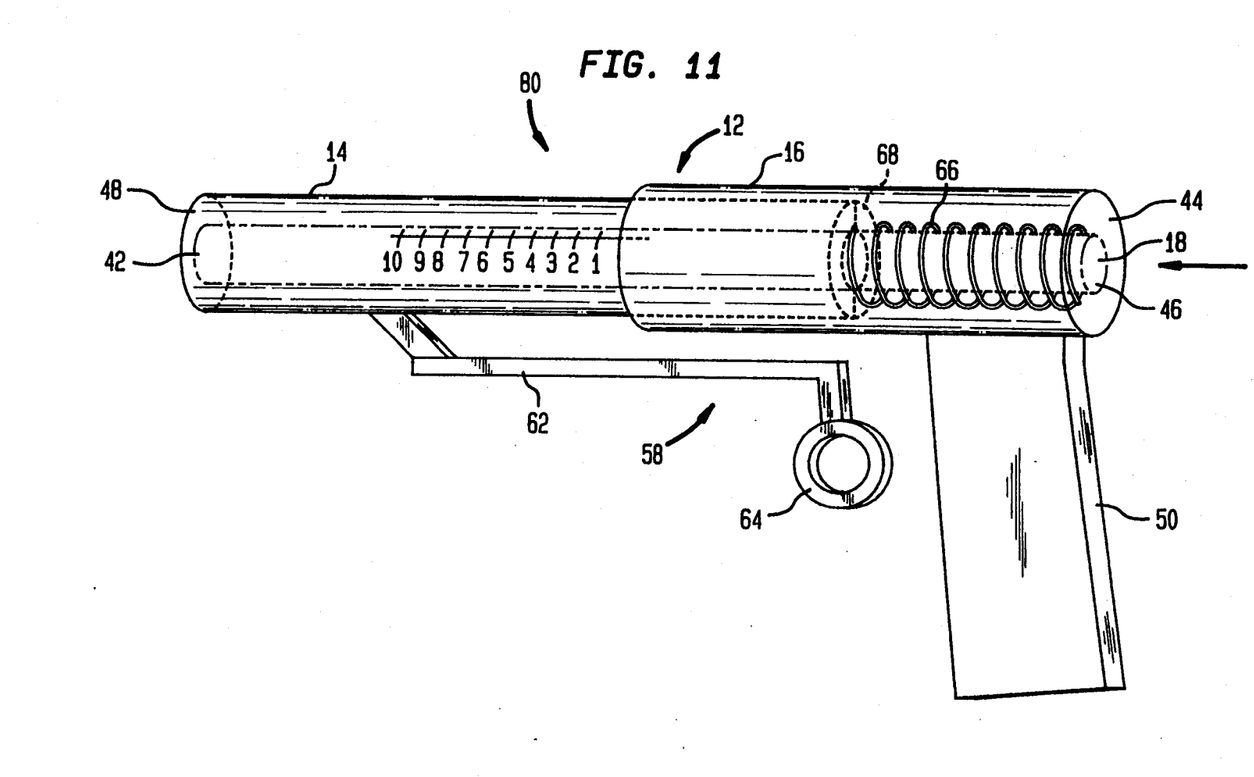
FIG. 11 illustrates a third embodiment of a surgical drill guide according to the invention.

FIG. 11 illustrates yet another embodiment of the drill guide 80 according to the invention. This embodiment is similar to that shown in FIG. 10 with different added features. The drill guide 80 shown in FIG. 11 has a trigger 58 which includes a long member 62 connected to the inner segment 14 and extending towards the handle 50. An eyelet 64 is formed at the end of this member 62 which makes it easier to retract the inner segment 14 using a single finger. The drill guide 80 is also shown with a spring 66 positioned within the outer segment 16. As shown, the spring 66 is a helical compression spring positioned between the inner side of the end 44 of the outer segment 16 and an end 68 of the inner segment 14. The spring 66 biases the inner segment 14 into its extended position.

Figure 12A:
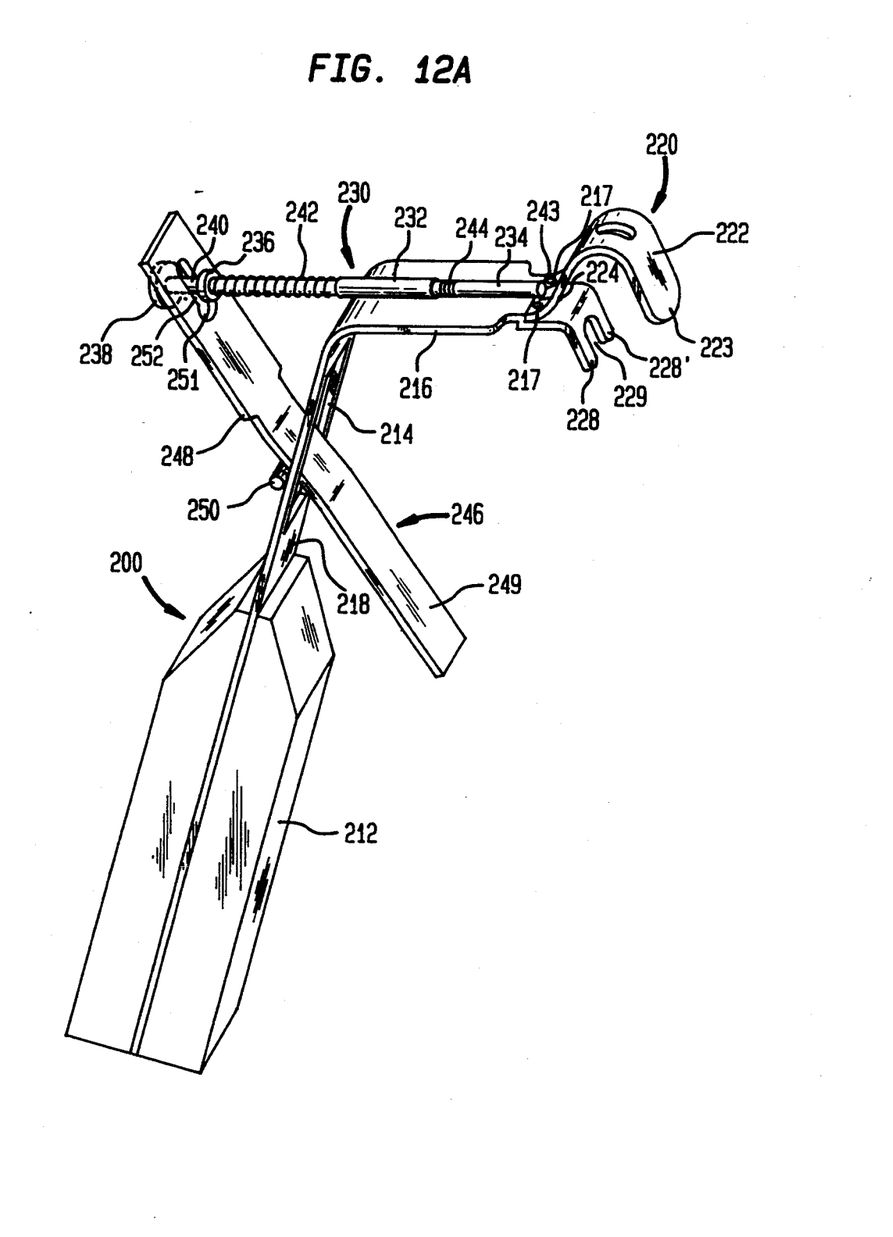
FIGS. 12A–12B illustrate a fourth embodiment of a surgical drill guide according to the invention.
Figure 12B:
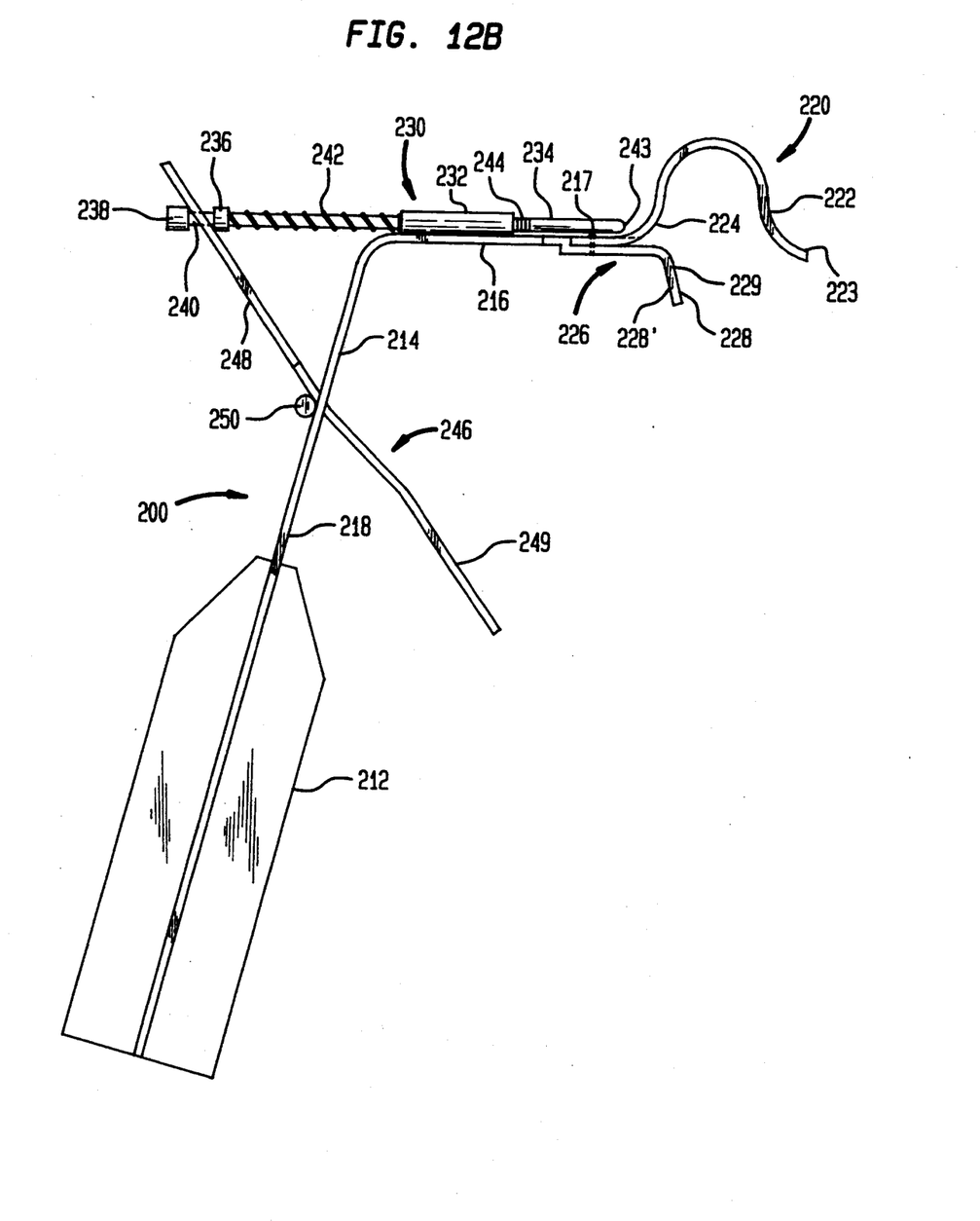

Another surgical drill guide 200 is shown in FIGS. 12A-B which is particularly suited for drilling into the zygomaticofrontal and infraorbital bones. The surgical drill guide and retractor 200 comprises a handle 212 from which a substantially L-shaped member 214 extends. The L-shaped member has a first short leg 216 and a second long leg 218. The long leg 218 extends from the handle 212.

A major retractor 220 is provided at the end of the short leg 216 in the form of an arcuate member. In the embodiment shown in FIGS. 12A-B, the major retractor 220 is demountably attached to the short leg 216 by screws 217 or by means of some other similar fastener. As illustrated, the major retractor 220 is about ⅜" wide, arcuate in shape, and has a slight concavity 222 near its tip 223. This shape allows the major retractor to be inserted around and behind a bone, such as the infraorbital bone, where it rests securely. This shape also results in the major retractor 220 being sloped away from the eyeball, thus putting less pressure on the eyeball itself. At the end of the major retractor 220 where it extends from the short leg 216, the major retractor 220 has an aperture 224, the purpose of which will be apparent later.

Figure 12C:
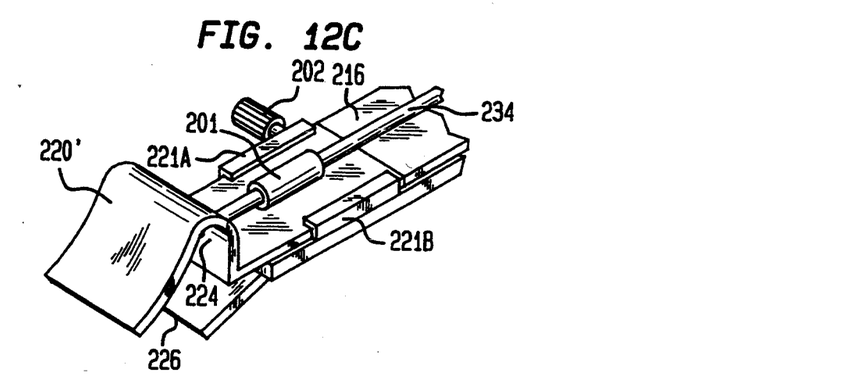
FIGS. 12C–12G illustrate the surgical drill guide of FIGS. 12A–12B with an adjustable, demountable major retractor.
Figure 12D:
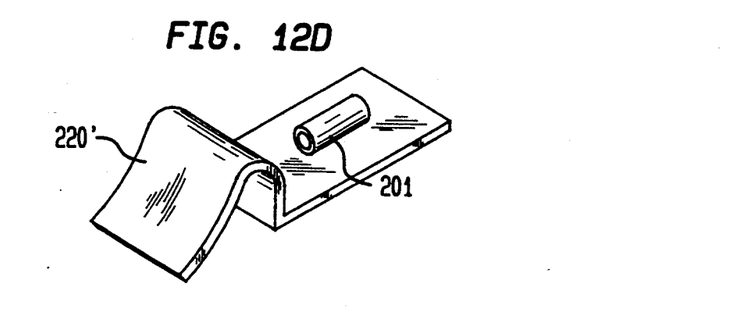
Figure 12E:
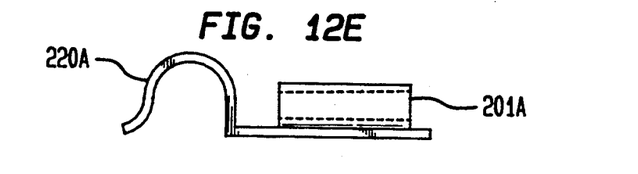
Figure 12F:
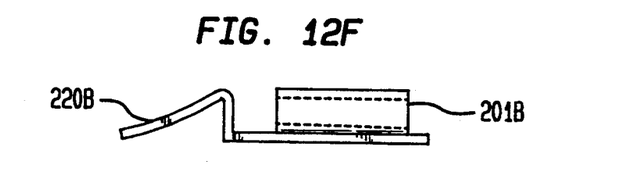
Figure 12G:
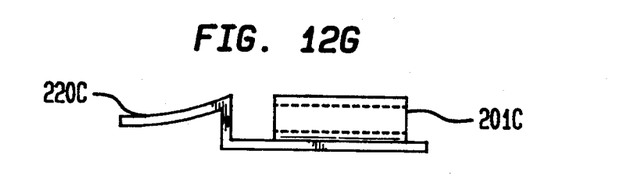

Another demountable, adjustable major retractor 220', having a second outer sleeve 201 into which the inner sleeve 234 is inserted, is shown in FIGS. 12C-12D. In this embodiment, the minor retractor 226 is preferably fixed. The demountable retractor 220' slides between C-shaped clamps 221A and 221B and may be adjusted to a desired extension from the short leg 216 and then secured by the knurled screw 202. FIGS. 12E-12G show demountable, adjustable major retractors 220A, 220B and 220C having different shapes which may be attached to the drill guide 200. The variety of shapes provides greater flexibility of applications for the drill guide 200.

A minor retractor 226 also extends from the short leg 216 at approximately the same location as the major retractor 220. The minor retractor 226 is welded to the bottom of leg 216 as illustrated, or may be attached by means of a universal joint (not shown) which permits adjustment of its position. The minor retractor 226 extends in a direction substantially opposite to the initial direction of the major retractor 220. When inserted into an incision, the major retractor 220 and minor retractor 226 cooperate so as to provide an opening effect thereby retracting the sides of the incision. The minor retractor 226 is much shorter than major retractor 220 and is bifurcated resulting in two fingers 228,228' separated by the bifurcation 229. The purpose of this structure is to enable the minor retractor 226 to be inserted around any nerves which might be located in the 5 region of the incision.

Mounted on top of the short leg 216 is a plunging mechanism 230. The plunging mechanism 230 comprises an outer sleeve 232 and an inner sleeve 234. Each of these sleeves has a through-going, longitudinal bore. The inner sleeve 234 is slidably positioned within the through-going bore of outer sleeve 232 so that it may slide in the longitudinal direction within outer sleeve 232. At one end of the inner sleeve 234, there are two circumferential shoulders 236 and 238 with a circumferential land 240 between them. A coil spring 242 is disposed between an edge of outer sleeve 232 and the shoulder 236 in order to resiliently bias the inner sleeve 234 into the retracted position shown in FIGS. 12A and 12B.

A lever 246 having first and second lever arms 248, 249 is mounted via hinge pin 250 on the long leg 218 of L-shaped member 214. The lever arm 248 includes a hole 251 and slot 252 arrangement by means of which lever arm 248 is mounted on the land 240 of inner sleeve 234. The hinge pin 250 is constructed in the form of a thumb screw so that it can be disassembled.

The combined surgical orbital drill guide and retractor 200 is used similarly to the other surgical drill guides. An incision is made in the region where a miniplate is to be placed and the bones are reduced to their correct anatomical positions. The surgeon then inserts the device 200 into the incision in such a manner that the major retractor 220 and the minor retractor 226 retract the sides of the incision. At the same time, the device 200 is manipulated so that the major retractor 220 is positioned on and behind the bone to act as a protective stop there while the minor retractor 226 is straddled over the lateral aspect of the incision and any major nerve in that region. With the device 200 in place the miniplate is then inserted over the reduced bone structure. In either event, after the miniplate and the device 200 are in place, with one finger the surgeon depresses the lever arm 249 so that it is brought into proximity with the handle 212. This causes the lever arm 248 to press against the shoulder 236 and the inner sleeve 234 slides forward through the bore of outer sleeve 232 and through the aperture 224 of major retractor 220 until the tip 243 abuts against a hole of the miniplate.

With the other hand, the surgeon now commences drilling by inserting a drill bit (not shown) through the longitudinal bore of the inner sleeve 234 and drilling through the bone. The drilling proceeds until the drill bit passes through the bone and reaches the tip 223 of the major retractor 220 located behind the bone.

In summary, a surgical drill guide has been described with a telescopic sleeve which may be easily adjusted with a single hand. The surgical drill guide may be used to perform all the various steps of bone plating as follows. After creating an incision and anatomic dissection, the surgical drill guide is inserted into position either before or after reduction of the bone segments. The bone plate is then adapted correctly and a drill bit is inserted into the bore of the drill guide. The drill guide is adjusted to the correct depth by urging a trigger towards the handle until the desired length of drill bit protrudes from the inner segment of the sleeve. A hole of the correct size is then drilled into the bone. If the drill guide is being used in the frontozygomatic or infraorbital region, then, after removal of the drill bit, a self-tapping screw is inserted into the bore of the drill guide and this is followed by the insertion of a screwdriver to securely tighten the screw. The process continues until the plate is completely screwed into place. Alternatively, when non-self tapping screws are to be utilized, after removal of the drill bit, a tap is inserted into the bore of the drill guide.

However, if the site of operation is in the cranium, mandible or other long bone, then after removal of the drill bit, a tap is inserted into the bore of the drill guide and is used to prepare the bone for receiving a screw. After the tap is removed, an appropriate size screw is inserted through the bore of the surgical drill guide followed by a screwdriver to tighten the screw. Prior to selection of a screw, the depth gauge on the sleeve of the drill guide is used to determined the correct screw length. These steps are repeated until the bone plate is completely secured.

Desirably, the drill bit and the tap which are used to make the hole in the bone are constructed with a wide shank followed by a narrower drilling or tapping portion. The bore of the inner sleeve is of sufficient width to receive the wide shank of the drill bit and tap. This will enable it also to accommodate the wider dimension of the screw head.

It will be apparent to those skilled in the art that the inventive surgical drill guide and retractor can also be used for wire fixation in addition to rigid internal fixation with a bone plate.

While the invention has been described by the reference to specific embodiments, this was for purposes of illustration only and should not be construed to limit the spirit or the scope of the invention.

I claim:

1. A surgical drill guide for restricting the penetration depth into a hole of a first end of an instrument having two ends, a second end having a larger girth than said first end, said drill guide comprising:

an adjustable length sleeve comprising,
  an outer telescopic segment having a first longitudinal bore, and
  an inner telescopic segment having a second longitudinal bore, and being retractably disposed within and protruding from only a first end of said first bore of said outer telescopic segment so that said first and second bores are linearly aligned to form a single longitudinal bore of said adjustable length sleeve,
  said inner and outer telescopic segments cooperating so that said inner telescopic sleeve is displaceable into and, out of only said first end of said first bore of said outer telescopic segment, and so that a displacement of said inner telescopic segment out of and into said first bore of said outer sleeve segment changes a longitudinal length of said adjustable length sleeve,
  wherein said single longitudinal bore of said adjustable length sleeve is dimensioned for slidably receiving an instrument therethrough, until a larger girth second end of the instrument abuts a first end of said adjustable length sleeve and a first end of the instrument protrudes from a second end of said adjustable length sleeve opposite said first end of said adjustable length sleeve,
  wherein said second end of said adjustable length sleeve is blunt,
  wherein said adjustable length sleeve is dimensioned such that said second end of said adjustable length sleeve from which the first end of the instrument protrudes is larger than a hole into which the instrument penetrates, and
a handle mounted to said adjustable length sleeve, said handle including trigger means for causing said inner telescopic segment to slidably retract into said outer telescopic segment to shorten said adjustable length sleeve so as to expose a preselected length of instrument inserted through said adjustable length sleeve,
wherein said penetration depth of said instrument into said hole is restricted to said preselected length.

2. The drill guide of claim 1, wherein said trigger means is hingedly mounted on said handle for scissoring movement in cooperation with said handle and said adjustable length sleeve.

3. The drill guide of claim 2 wherein said handle is connected to said inner segment, and
wherein said trigger means comprises a lever with first and second lever arms, said first lever arm interacting with said outer segment so that when said second lever arm is urged towards said handle, said first lever arm forces said outer segment to slide towards said inner segment thereby retracting said inner segment into said outer segment.

4. The drill guide of claim 1 wherein said adjustable length sleeve further comprises biasing means for biasing said inner telescopic segment into an extended position from said outer telescopic segment.

5. The drill guide of claim 4, wherein said biasing means is a compression spring disposed within said outer telescopic segment, between said inner segment and end of said outer segment.

6. The drill guide of claim 1 wherein said handle is attached to said outer segment and said trigger means is attached to said inner segment.

7. The drill guide of claim 1 wherein said trigger means is attached to said adjustable length sleeve for sliding movement in cooperation with said handle and said adjustable length sleeve.

8. The drill guide of claim 7 wherein said trigger means comprises substantially L-shaped member having a long leg, connected to said adjustable length sleeve, and a short leg, extending towards said handle.

9. The drill guide of claim 7 wherein said trigger means comprises a long member and an eyelet connected to said long member, said long member being attached to said adjustable length sleeve with said eyelet extending towards said handle.

10. The drill guide of claim 1, further comprising a depth gauge on an outer surface of said adjustable length sleeve.

11. The drill guide of claim 1 wherein said trigger means further comprises retaining means for retaining said inner segment at an adjusted extension from said outer segment.

12. The drill guide of claim 11 wherein said retaining means is a set screw.

13. The drill guide of claim 1 wherein said trigger means is disposed in the vicinity of said handle for single handed gripping and retracting of said inner segment into said outer segment.

14. The drill guide of claim 1, wherein said adjustable length sleeve further comprises a chamfered tip at said inner telescopic end.

15. The drill guide of claim 1, wherein said outer segment is dimensioned to receive said instrument but is smaller than said second end of said instrument.

16. The drill guide of claim 1, wherein said outer segment further comprises a stop which limits the insertion of said instrument into said single longitudinal bore to a particular length.

17. The drill guide of claim 1 further comprising retractor means for retracting at least one side of an incision.

18. The drill guide of claim 17 wherein said retractor means further comprises major and minor retractors extending in substantially opposite directions.

19. The drill guide of claim 17 wherein said retractor means further comprises means for demountably attaching said retractor means to said drill guide.

20. The drill guide of claim 17 wherein said retractor means further comprises means for extending said retractor means in a direction parallel to said inner segment.

21. The drill guide of claim 1 wherein said trigger means further comprises retractor means extending from said trigger means for retracting at least one side of an incision.

22. The surgical guide of claim 1, wherein said instrument is a drill bit.

23. A surgical drill guide for restricting penetration depth into a hole of a first end of an instrument having two ends, a second end having a larger girth than said first end, said guide comprising, an adjustable length sleeve comprising,
an outer telescopic segment having a first longitudinal bore, a first end and a second end,
an inner telescopic segment having a second longitudinal bore, and being retractably disposed within and protruding from only a first end of said first bore of said outer telescopic segment so that said first and second bores are linearly aligned to form a single longitudinal bore of said adjustable length sleeve,
said inner and outer telescopic segments cooperating so that said inner telescopic sleeve is displaceable into and out of only said first end of said first bore of said outer telescopic segment, and so that a displacement of said inner telescopic segment out of and into said first bore of said outer sleeve segment changes a longitudinal length of said adjustable length sleeve,
wherein said single longitudinal bore of said adjustable length sleeve is dimensioned for slidably receiving an instrument therethrough, until a larger girth second end of the instrument abuts a first end of said adjustable length sleeve and a first end of the instrument protrudes from a second end of said adjustable length sleeve opposite said first end of said adjustable length sleeve,
wherein said second end of said adjustable length sleeve is blunt,
stop means, located at said first end of said adjustable length sleeve for limiting a length of the instrument received in said single longitudinal bore to a particular length, and
a handle on which said adjustable length sleeve is mounted, said handle comprising trigger means for slidably retracting said inner telescopic segment into said outer telescopic segment so as to expose a preselected length of instrument inserted through said adjustable length sleeve.

24. The surgical guide of claim 23, wherein said instrument is a drill bit.

25. A surgical drill guide comprising
a telescopic sleeve comprising an inner telescopic segment having a first longitudinal bore and an outer telescopic segment having a second longitudinal bore, said inner telescopic segment being slidably mounted in said outer telescopic segment,
a first opening at an end of said outer telescopic segment,
a second opening at an end of said inner telescopic segment,
said first and second bores being longitudinally aligned to form a single longitudinal bore, passing through said inner and outer telescopic segments and connecting said first and second openings together, said single longitudinal bore being dimensioned for slidably receiving an instrument therethrough,
a handle on which said telescopic sleeve is mounted, said handle including trigger means for causing said inner telescopic segment to slidably retract into said outer telescopic segment so as to expose, at said second opening, a preselected length of instrument inserted through said single longitudinal bore of said telescopic sleeve, and
a retractor means attached to said telescopic sleeve for retracting at least one side of an incision, said retractor means further comprising means for demountably attaching said retractor means to said drill guide.

* * * * *